United States Patent
Voth

(10) Patent No.: US 8,920,745 B2
(45) Date of Patent: Dec. 30, 2014

(54) ASEPTIC STERILIZATION UNIT FOR CLEAN ROOM ON BLOWING WHEEL

(75) Inventor: Klaus Voth, Obertraubling (DE)

(73) Assignee: Krones AG, Neutraubling (DE)

( * ) Notice: Subject to any disclaimer, the term of this patent is extended or adjusted under 35 U.S.C. 154(b) by 0 days.

(21) Appl. No.: 13/236,623

(22) Filed: Sep. 19, 2011

(65) Prior Publication Data

US 2012/0070340 A1 Mar. 22, 2012

(30) Foreign Application Priority Data

Sep. 20, 2010 (DE) .......................... 10 2010 045 832

(51) Int. Cl.
*A61L 2/18* (2006.01)
*A61L 2/22* (2006.01)
*B29C 49/46* (2006.01)

(52) U.S. Cl.
CPC ........... *A61L 2/22* (2013.01); *B29C 2049/4679* (2013.01); *A61L 2202/23* (2013.01); *B29C 2049/4697* (2013.01); *B29C 49/46* (2013.01); *A61L 2/18* (2013.01)
USPC ........................................... 422/302; 422/28

(58) Field of Classification Search
CPC .................................. A61L 2/18; A61L 2/20
USPC ................................................... 422/28, 292
See application file for complete search history.

(56) References Cited

U.S. PATENT DOCUMENTS

| | | | |
|---|---|---|---|
| 6,562,281 B1 * | 5/2003 | Marchau et al. ............... | 264/532 |
| 2010/0089009 A1 * | 4/2010 | Till .................... | 53/452 |
| 2011/0133369 A1 | 6/2011 | Martini et al. | |

FOREIGN PATENT DOCUMENTS

| | | |
|---|---|---|
| DE | 10 2007 017 938 A1 | 10/2008 |
| DE | 20 2009 010 813 U1 | 1/2010 |
| EP | 0 741 080 A1 | 11/1996 |
| EP | 2 246 176 A1 | 11/2010 |
| EP | 2 368 835 A1 | 9/2011 |
| EP | 2 388 127 A2 | 11/2011 |
| WO | 2010/020529 A2 | 2/2010 |

OTHER PUBLICATIONS

German Search Report dated Aug. 4, 2011, issued in counterpart German Application No. 10 2010 045 832.5.
European Search Report dated Dec. 22, 2011, issued in counterpart European Application No. 11181565.0.

* cited by examiner

*Primary Examiner* — Sean E Conley
(74) *Attorney, Agent, or Firm* — Novak Druce Connolly Bove + Quigg$^{LLP}$

(57) ABSTRACT

An apparatus for the treatment of plastics material containers includes at least one movable support which is arranged in an isolator room to which a sterilization agent is capable of being supplied. The isolator room is constructed in at least two parts, and a first boundary of the isolator room is fixed in position during a movement of the movable support, while a second boundary of the isolator room is connected to the apparatus in such a way that it is suitable, during a movement of the movable support, for following this movement. The apparatus has at least one device for supplying the sterilization agent into the isolator room. The supplying device is suitable for acting with the sterilization agent upon the parts of the apparatus movable relative to this device and situated inside the isolator room.

9 Claims, 3 Drawing Sheets

ASEPTIC STERILIZATION UNIT FOR CLEAN ROOM ON BLOWING WHEEL

CROSS-REFERENCE TO RELATED APPLICATION

This application claims the benefit of priority of German Patent Application No. 10 2010 045 832.5, filed Sep. 20, 2010, pursuant to 35 U.S.C. 119(a)-(d), the disclosure of which is incorporated herein by reference.

TECHNICAL FIELD

The present disclosure relates to an apparatus for the treatment of plastics material containers, the apparatus having at least one movable support which is arranged in an insulator room to which a sterilization agent is capable of being supplied. In addition, the disclosure relates to a method of sterilizing an insulator room of an apparatus for the treatment of plastics material containers, with at least one movable support which is arranged in an insulator room to which a sterilization agent is supplied.

BACKGROUND

Apparatuses for the treatment of plastics material containers have long been known from the prior art. An example of an apparatus of this type is blow moulding machines for shaping plastics material pre-forms to form plastics material containers. Other apparatus of this type are for example ovens (for example microwave ovens) for heating containers or conveying star wheels for the conveying of the plastics material containers. Apparatus of this type usually have at least one movable support on which devices for receiving the plastics material containers are arranged. As a rule, blow moulding machines have for example a plurality of movable blow moulds which in each case form a cavity inside which the plastics material pre-forms are capable of being shaped into containers and inside which pre-forms of plastics material (plastics material pre-forms) are expanded to form plastics material containers. Blow moulding machines of this type are usually rotating, substantially circular plants. In this case they receive plastics material pre-forms at a specified position, and during the rotation and the exceeding of a specified sector of the latter they form the plastics material containers which are removed in turn at a specified position.

Constantly greater demands with respect to the throughput and the quality of the containers produced or treated are placed upon blow moulding machines of this type and also, on the other hand, other apparatus for the treatment of plastics material containers. In particular, the hygiene and thus the sterility of the containers are required in the field of the filling of foodstuffs. As a result of the sterilization of the relatively small plastics material pre-forms and the subsequent sterile (aseptic) treatment of these plastics material preforms by way of the blow moulding process to form the desired container until the filling procedure, it is possible not only to accelerate the entire process but also to reduce the quantity of sterilization agent used, since it is necessary to sterilize only the surface of the pre-forms which are significantly smaller than the finished containers. In this way, not only can the quantity of sterilization agent be reduced, however, but the process can also be significantly simplified. It is thus possible for example, when using vaporized sterilization agent solutions (such as for example alcohols, chlorinated water, hypochlorous acid, ozone solution, hydrogen peroxide, peracetic acid and others), for excess sterilization agent to be easily removed again. The final residues of the sterilization agent also escape during the heating of the pre-forms for the blow moulding process at the latest, in which case of course the appropriate safety aspects in the case of peroxides have to be observed. A subsequent complicated cleaning and drying of the finished containers before the filling procedure is not necessary. In this way, despite the additional effort to ensure sterility during the entire production process, it is possible to increase the efficiency significantly.

It is important for a high degree of efficiency that only as small as possible a number of the apparatus for the treatment of containers should have the aseptic conditions. Since the maintenance of these sterile conditions is quite costly, it has been found to be advantageous to keep sterile only the region of the apparatus for the treatment of containers in which the sterile pre-forms or containers are present. An apparatus of this type is disclosed for example in WO 2010/020529 A2.

A blow moulding machine is disclosed in DE 10 2007 017 938 A1, which is situated completely in a sterile clean room (isolator room). In order to be able to maintain sterility even over a prolonged period in running operation, radiation sources which act upon the parts to be sterilized with radiation in order to kill germs, are arranged on the blowing wheel and along the conveying path of the pre-forms or containers respectively.

The use of gases or aerosols for the sterilization of clean rooms, however, affords some advantages as compared with a sterilization by means of radiation. In this way, in particular when sterilization gases are used, on account of their considerable diffusion capacity it is possible to penetrate even into areas which are inaccessible to radiation sources. By way of example, when UV lamps are used for sterilization, specific areas of the blowing station are exposed for longer to the light radiated by these lamps than are other areas. This is based inter alia on the shape of the individual blowing stations which cast a shadow into specific areas at least for a time. In these areas it is possible in some cases for germs to settle, multiply and lead to contamination.

It may therefore be desirable to make available an apparatus for the treatment of plastics material containers, wherein the apparatus has at least one movable support which is arranged in an isolator room to which a sterilization agent is capable of being supplied. The isolator room may comprise movable and immovable elements and the apparatus has devices for supplying a sterilization agent into the isolator room, which devices sterilize parts—movable relative to these devices in each case—inside the isolator room by acting upon them with a sterilization agent.

SUMMARY

According to various aspects of the disclosure, an apparatus for the treatment of plastics material containers has at least one movable support which is arranged in an isolator room to which a sterilization agent is capable of being supplied, the isolator room being constructed in at least two parts and a first boundary of the isolator room being fixed in position during a movement of the movable support, whereas a second boundary of the isolator room is connected to the apparatus or the blowing station in such a way that it is suitable, during a movement of the movable support, for following this movement, in which case the apparatus has at least one device for supplying the sterilization agent into the isolator room, which device is suitable for acting with the sterilization agent upon the parts of the apparatus movable relative to this device and situated inside the isolator room.

As a result, it is possible for the sterilization agent to be conveyed as a gas or fine spray (aerosol) to the areas of the apparatus or the blow moulding machine to be disinfected. There is the possibility of also introducing the sterilization agent heated into the interior of the isolator room. In this case the device for supplying the sterilization agent into the isolator room may be designed in such a way that during the movement of the apparatus or the movable support it acts upon those parts inside the isolator room (clean room) substantially uniformly with sterilization agent, which are arranged so as to be movable relative to the device. In this way for example, with a blowing wheel during one revolution all the parts of the blowing wheel present in the isolator room are conveyed past a stationary device for supplying the sterilization agent into the isolator room and are acted upon with the sterilization agent. In the same way, it is possible for the device for supplying the sterilization agent into the isolator room to be arranged in a movable manner on the movable support, for example the blowing wheel, in order to act with the sterilization agent upon the stationary parts of the isolator room during the movement, for example one revolution of the blowing wheel. In the same way, a plurality of devices for supplying the sterilization agent into the isolator room are possible, in which case these can be arranged independently of one another both in a stationary manner and in a movable manner with respect to the at least one device for receiving the plastics material containers (for example a blowing station).

In order to remove residues of the sterilization agent in the interior of the isolator room after a sterilization procedure, which could possibly have penetrated into the plastics material containers produced, conveyed or treated, it is also possible to introduce other substances such as for example a washing solution by way of the device for supplying the sterilization agent into the isolator room. In the same way for example, the sequential use of a plurality of different sterilization agents (for example bactericidal, sporicidal, fungicidal and virucidal sterilization agents or combinations thereof) is possible.

The apparatus according to the disclosure is, in particular, a blow moulding machine. The apparatus according to the disclosure could also, however, be a heating device which heats plastics material pre-forms or, on the other hand, a filling device for filling containers. In addition, an apparatus in accordance with the disclosure would also be capable of being used for conveying devices which convey plastics material containers such as plastics material pre-forms or plastic bottles. In general, an apparatus in accordance with the disclosure is capable of being used in those plants which have movable and, in particular, rotating parts as well as a clean room.

In an exemplary embodiment of the apparatus the device for supplying the sterilization agent into the isolator room has a plurality of nozzles. On account of these nozzles it is possible on the one hand for the sterilization medium to be introduced in a preferential direction into the isolator room and thus to ensure that even areas of the isolator room which are accessible only with difficulty are acted upon with the sterilization medium. In addition, by means of these nozzles it is possible for liquid sterilization agents and the solutions thereof to be finely distributed in the interior of the isolator room and to form an aerosol or spray. This remains stable for a long time, as a result of which, during a movement of the movable support, an extremely uniform distribution of these fine drops of aerosol is achieved on account of the air swirls occurring during the movement in the interior of the clean room. This ensures that the parts to be sterilized are acted upon with the sterilization agent in a uniform manner. It is also possible for the nozzles to be made pivotable or rotatable in order to impart an altered, preferred flow direction to the discharged sterilization agent.

In an exemplary embodiment of the apparatus the movable part of the boundary of the isolator room (isolator room boundary) and the stationary part of the boundary of the isolator room are closed off from the environment by means of a seal arranged between these boundaries, in such a way that a movement of these boundaries with respect to each other is possible, but penetration by contamination, however, is eliminated. In principle, any suitable type of seal can be used for delimiting the interior of the isolator room off from the non-sterile environment at the same time as the movable storage of the movable part of the isolator room boundary with respect to the stationary part of the isolator room boundary. On account of the large sealing area and the constant movement, which potentially causes abrasion and thus increased wear of the sealing elements, seals may be preferred which use a blocking medium. It may be preferable for so-called surge chambers to be used.

Devices fixed in position for supplying the sterilization agent to the isolator room have been found to be particularly suitable for the most efficient sterilization of the parts of the apparatus present in the interior of the clean room. In an exemplary embodiment of the apparatus at least some of the devices for supplying the sterilization agent to the isolator room are thus arranged fixed in their position. These may be arranged in such a way that during a complete movement cycle all the parts of the apparatus present in the interior of the clean room pass at a slight distance the devices for supplying the sterilization agent to the isolator room and, in this way, these parts can be acted upon directly with the sterilization agent. In this case the devices for supplying the sterilization agent can be arranged on a stationary support or for example also on a stationary boundary wall of the isolator room.

Only with an individual stationary device for supplying the sterilization agent to the isolator room does the problem arise that the stationary parts of the isolator room are frequently acted upon with the sterilization agent to only an inadequate degree. In embodiments of apparatus—designed in a particularly complicated manner—for the treatment of plastics material containers, the fine distribution of the sterilization agent in the form of a spray in the interior of the isolator room, as already described, and a subsequent swirling of this spray also do not necessarily ensure an adequately uniform distribution. An adequate sterilization of the inaccessible areas could be achieved for example by occasional separate sterilization. Since this is very time-consuming and requires a stoppage of the entire plant, devices may be advantageous which also ensure an adequate sterilization of the stationary parts.

In an exemplary embodiment of the apparatus, at least some of the devices for supplying the sterilization agent into the isolator room are therefore arranged in a movable manner. If these movably arranged devices for supplying the sterilization agent to the isolator room are situated for example on the movable support (for example the blowing wheel), during one movement cycle they pass the entire stationary part of the isolator room boundary and can act upon the latter with sterilization agents. It may be preferable, in some aspects for these devices for supplying the sterilization agent to the isolator room also to be designed in the form of nozzles. It may be advantageous for the aforesaid devices for supplying the sterilization agent to be arranged in such a way that they apply the sterilization agent at least along the complete height of the isolator room.

In the case of a design of this type, however, there is the problem of supplying the sterilization agent in a continuous manner to the movable devices for supplying the sterilization agent to the isolator room. In an exemplary embodiment of the apparatus the movably arranged devices for supplying the sterilization agent into the isolator room are therefore connected to a rotary distributor which is suitable for supplying the sterilization agent to the devices. This ensures in a simple manner that the devices for supplying the sterilization agent into the isolator room are continuously and adequately supplied with sterilization medium.

In an exemplary embodiment of the apparatus the apparatus has a central reservoir for the sterilization agent. Both the movable and the stationary devices for supplying the sterilization agent into the isolator room can be supplied with the sterilization agent from this reservoir. As already mentioned, the supply to the movable devices may be carried out by means of a rotary distributor.

The movable support of the apparatus may be a substantially circular apparatus. In an exemplary embodiment of the apparatus the movable support is therefore a blowing wheel with at least one blowing station, which is arranged at least in part in the interior of the isolator room. This embodiment in the form of an approximately circular blowing wheel simplifies the geometry of the isolator room and at the same time reduces areas in the interior of the isolator room which are accessible to the sterilization agent only with difficulty. It may be advantageous for the isolator room to have an annular or toroidal shape, in which case the blowing stations are conveyed at least in part inside the isolator room.

As already described, the sterilization agents are, in some aspects, substances capable of being easily distributed. In an exemplary embodiment the sterilization agent is present in the form of a gas or liquid at the moment of injection into the isolator room. The sterilization agent is capable of being easily distributed in the form of both a gas and a liquid (for example, in the form of a finely distributed aerosol). In particular, during a movement of the support on which the individual devices for the treatment of plastics material containers are arranged, it can therefore be finely distributed by the air swirling which occurs. This ensures that the areas in the interior of the isolator room, which are directly accessible only with difficulty when the sterilization agent is injected, are also acted upon with the sterilization agent in an adequate manner.

In specific cases it is necessary to ensure additional air movements for the further distribution of the sterilization agent in the interior of the isolator room of the apparatus. In an exemplary embodiment the isolator room therefore has inlets for compressed air, which are suitable for permitting a high-pressure cleaning of the isolator room. On account of these inlets it is likewise possible for a slight over-pressure, which prevents non-sterile gas from diffusing into the interior of the isolator room and thus contaminating it, to be produced in the interior of the isolator room.

An aspect of the disclosure is a method of sterilizing an insulator room of an apparatus for the treatment of plastics material containers, with at least one movable support which is arranged in an insulator room to which a sterilization agent is supplied, in which case the isolator room is designed in at least two parts and a first boundary (boundary device) of the isolator room does not move during a movement of the movable support, whereas a second boundary (boundary device) of the isolator room is connected to the apparatus in such a way that during a movement of the movable support it follows this movement and these movements are coupled (in particular in a mechanical manner), in which case at least one device is provided for supplying the sterilization agent into the isolator room, by which the parts of the apparatus movable relative to this device and present inside the isolator room are acted upon with the sterilization agent.

On account of this method it is possible in a very simple and efficient manner for the interior of the isolator room to be acted upon with the sterilization agent. In this way, during a movement cycle of the movable support almost all the parts movable relative to the supply device can be acted upon with the sterilization agent. It may be advantageous for the aforesaid relative movement to be caused by a movement of a support on which the apparatus for the treatment of plastics material containers is arranged (for example one or more blowing stations). There is likewise the possibility of also introducing the sterilization agent heated into the interior of the isolator room. By way of example, $H_2O_2$, peracetic acid or other sterilization agents or the aqueous solutions thereof can be set in the gas phase before being introduced into the isolator room.

Further advantages, aims, and properties of the present disclosure are explained with reference to the following description of the accompanying drawings, in which by way of example an apparatus according to the disclosure is illustrated in the example of a blow moulding machine with at least one blowing station for shaping plastics material pre-forms to form plastics material containers, the blowing station being arranged on a movable support and the blow moulding machine having an isolator room to which a sterilization agent is capable of being supplied.

Further advantages and embodiments will become evident from the attached drawings.

DETAILED DESCRIPTION

Figure 1:
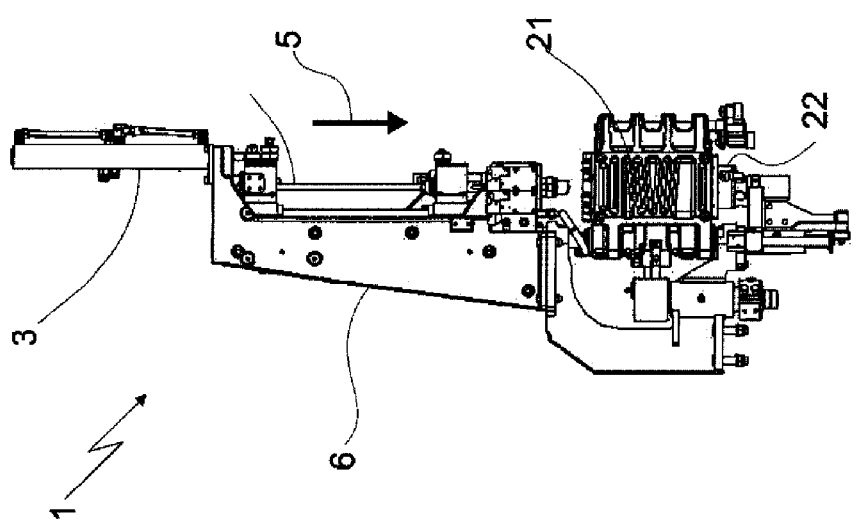
FIG. 1 shows a blowing station according to the prior art.

FIG. 1 shows a blowing station 1 according to the prior art for shaping plastics material pre-forms to form plastics material containers. In this case a plurality of blowing stations 1 of this type is arranged on a rotatable blowing wheel (not shown). The reference number 3 in FIG. 1 shows a drive device 3 which is used for actuating the stretch rod 4, i.e., for moving the stretch rod 4 in the extension direction 5. The reference number 6 relates to a support 6 on which the stretch rod arrangement 4 is arranged. In this case the blowing station has two lateral parts 20, 21 (cf. FIG. 2) and a base part 22, which jointly form a cavity in which plastics material pre-forms are capable of being expanded into plastics material containers.

Figure 2:
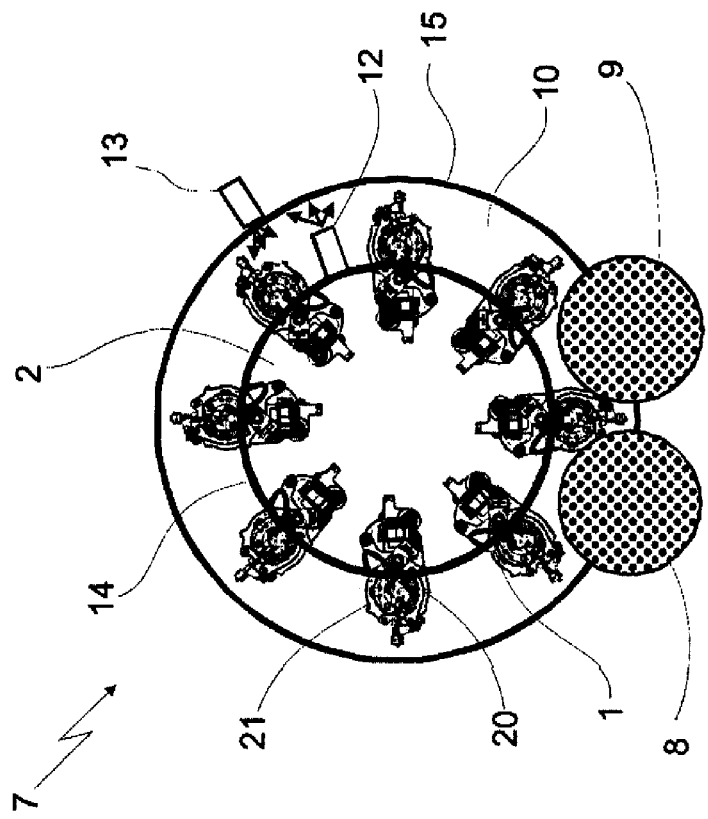
FIG. 2 is a diagrammatic view of an exemplary blow moulding machine with a supply device, a removal device, and an isolator room into which a sterilization agent is capable of being supplied by means of suitable devices.

FIG. 2 is a diagrammatic view of a blow moulding machine 7 with a supply device 9, a removal device 8, a plurality of blowing stations 1 and an isolator room 10 into which a sterilization agent is capable of being supplied by means of suitable devices 12, 13. The movable support 2 of the blow moulding machine 7 on which the blowing stations 1 are arranged is designed in the form of a circular blowing wheel 2. A movable device 12 and a stationary device 13 for supplying the sterilization agent are shown in each case at positions by way of example in FIG. 2. During a rotation of the part 14 of the isolator room 10 situated radially on the inside, all the movable elements (such as for example the blowing stations 1) pass the stationary device 13 for supplying the sterilization agent and can be acted upon with the sterilization agent. The movable device 12 for supplying the sterilization agent can act upon the stationary part 15 of the isolator room 9 situated radially on the outside with the sterilization agent during one revolution. In this case the aforesaid device 12 for supplying the sterilization agent is arranged between two blowing stations 1.

Figure 3:
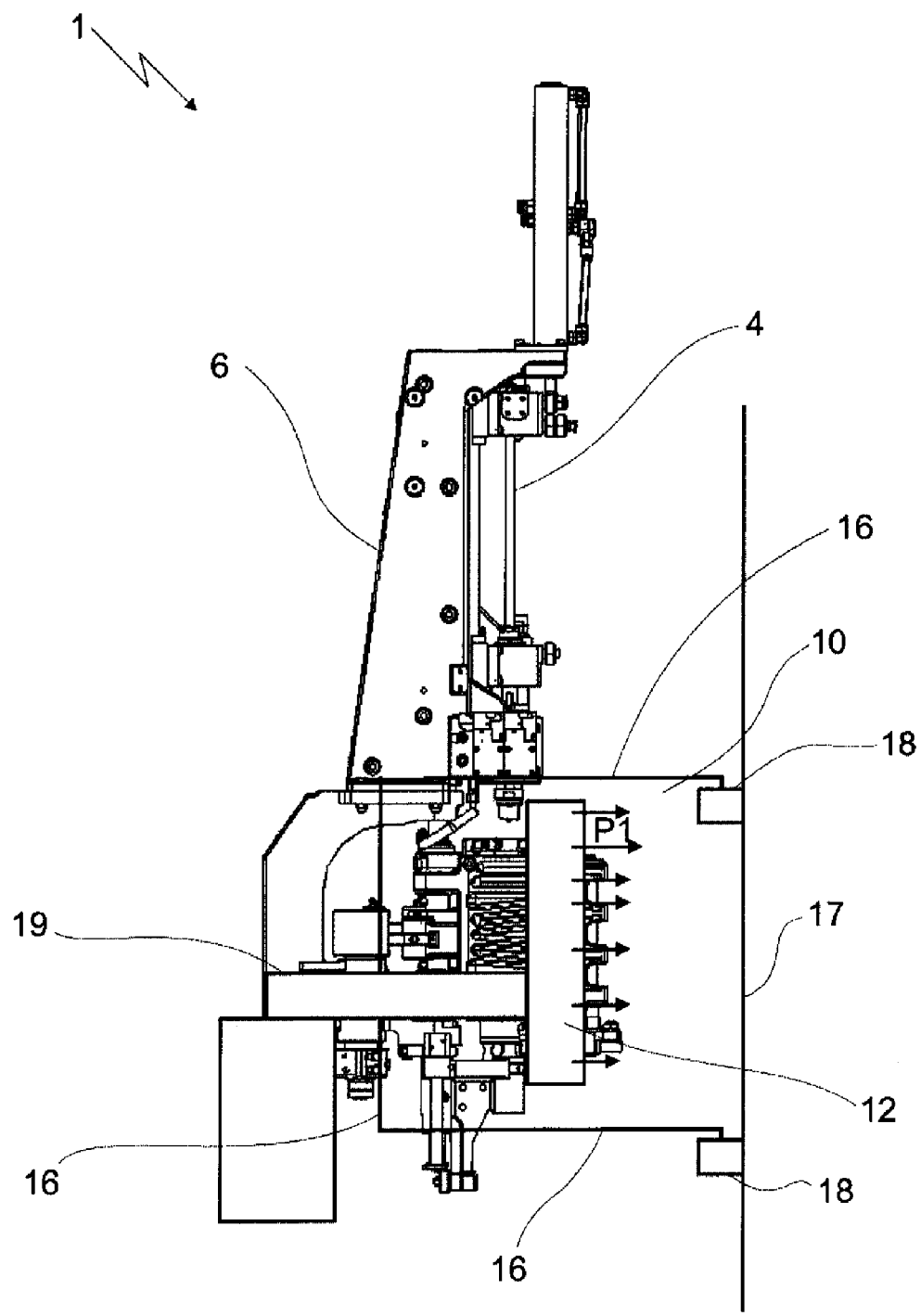
FIG. 3 is a diagrammatic illustration of an exemplary blowing station which is situated in part in the interior of an isolator room, a sterilization agent being capable of being supplied to the isolator room by means of a movable device.

FIG. 3 is a diagrammatic illustration of a blowing station 1 which is situated in part in the interior of an isolator room 9, in which case a sterilization agent is capable of being supplied (arrows P1) to the isolator room 9 by means of a movable device 12. In the example shown the isolator room 9 is closed off on three sides by boundaries 16 which follow movements of the blowing wheel 2. They are movable by means of seals 18 with respect to the stationary boundary 17 of the isolator room 9, but they are mounted in a gas-tight manner. In the same way the stretch rod 4 is screened off from the isolator room 9 by means of a seal (for example a folding bellows) in order to maintain the sterility of the isolator room 9 when the stretch rod 4 is lowered from the non-sterile region into the interior of the plastics material pre-form and thus into the sterile region (namely the interior of the isolator room 9). It may be preferable, in some aspects, for the at least one device 12, 13 for supplying the sterilization agent to be arranged in the interspaces between the blowing stations 1.

The sterilization agent can be supplied to this device 12, 13 by way of a pipeline system 19. Metering or throttling devices are optionally present in the line system. The sterilization agent can be discharged out of the device 12, 13 by way of outlet openings and can reach the interior of the isolator room 9 and also the inner surfaces of the boundaries 16, 17. The direction in which the sterilization agent is discharged can be pre-set by way of the shape and orientation of the outlet openings.

In the same way, the degree of atomization can also be preset by way of nozzles (not shown), so that it is possible to produce a fine aerosol of the sterilization agent which remains in the gas phase for a prolonged period without being deposited completely. In order to prevent residues of the aerosol from remaining and possibly reaching the interior of the produced plastics material containers after a sterilization procedure, it is possible for other substances such as for example a washing solution also to be introduced into the isolator room by way of the device 12, 13 for supplying the sterilization agent. In addition, the use of a multiplicity of different sterilization agents (for example bactericidal, sporicidal, fungicidal and virucidal sterilization agents or combinations thereof) is thus possible.

Figure 4:
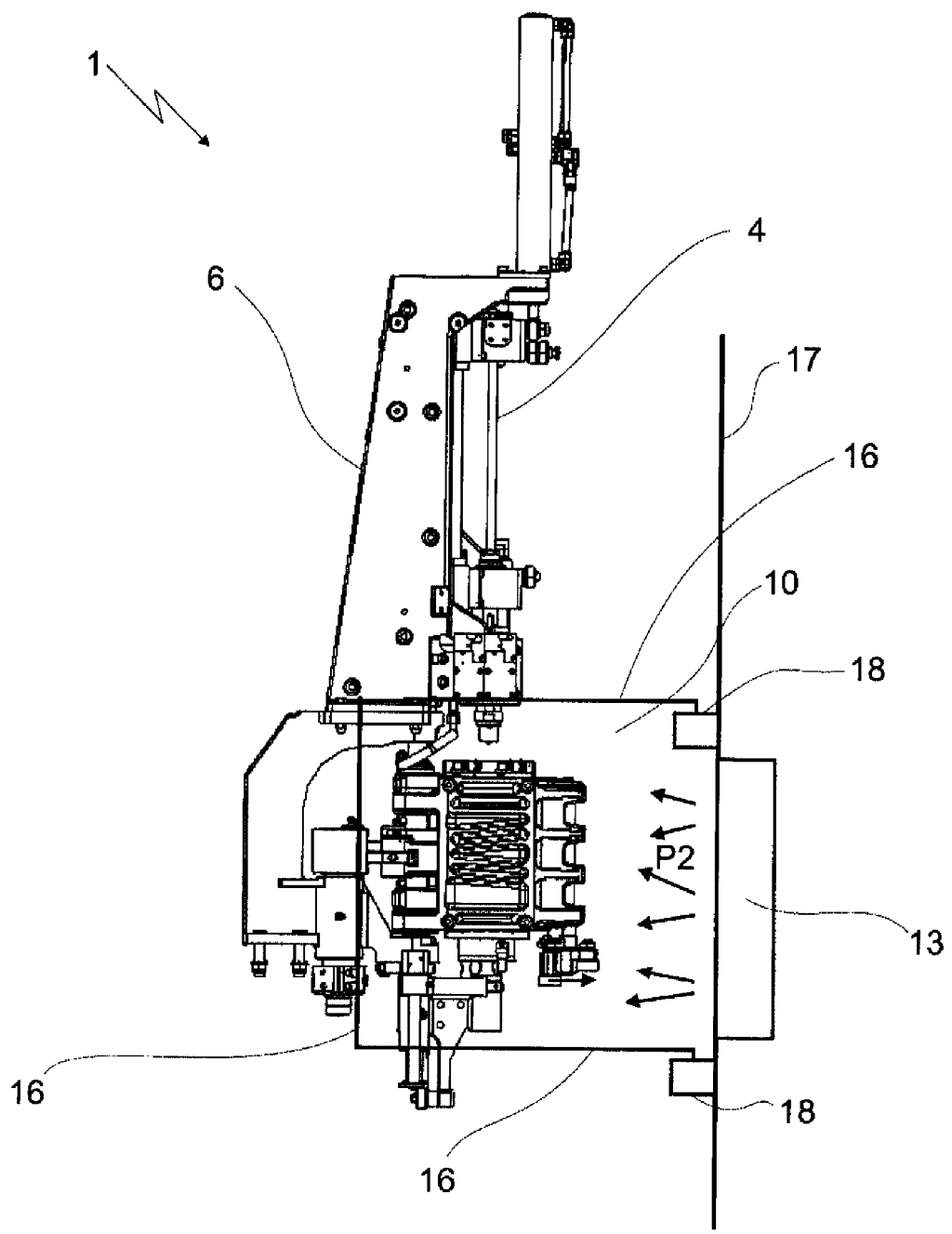
FIG. 4 is a diagrammatic illustration of an exemplary blowing station which is situated in part in the interior of an isolator room, a sterilization agent being capable of being supplied to the isolator room by means of a stationary device.

FIG. 4 is a diagrammatic illustration of a blowing station 1 which is situated in part in the interior of an isolator room 9, in which case sterilization agents are capable of being supplied to the isolator room 9 by means of a stationary device 13 (arrows P2). As also shown in FIG. 3, the isolator room 9 is closed off on three sides by boundaries 16 which follow the movements of the blowing wheel 2. A stationary device 13 for supplying the sterilization agent is arranged in the region of the stationary boundary 17 of the isolator room 9. The sterilization agent can be supplied to this stationary device 13 by way of a pipeline system (not shown). Opposite the movable boundaries 16 of the isolator room 9 the stationary boundary 17 is mounted in a gas-tight manner by means of at least one seal 18 in such a way that a movement of the blowing wheel 2 is possible, for example, without undue energy losses. The sterilization agent can be discharged out of the stationary device 13 by way of discharge openings and can be applied directly to the movable parts—moved past the stationary device 13 during a rotation of the blowing wheel 2—in the interior of the isolator room 9. The stationary discharge openings can also be nozzles which make it possible to pre-set the direction in which the sterilization agent is sprayed. In addition, the degree of atomization can be pre-set by way of the nature or the setting of the nozzles. It is also possible for the nozzles to be made pivotable or rotatable in order to impart an altered preferred flow direction to the discharged sterilization agent.

It will be apparent to those skilled in the art that various modifications and variations can be made to the device for processing preforms of the present disclosure without departing from the scope of the invention. Throughout the disclosure, use of the terms "a," "an," and "the" may include one or more of the elements to which they refer. Other embodiments of the invention will be apparent to those skilled in the art from consideration of the specification and practice of the invention disclosed herein. It is intended that the specification and examples be considered as exemplary only.

What is claimed is:

1. An apparatus for the treatment of plastics material containers, comprising:
    an isolator room to which a sterilization agent is capable of being supplied;
    at least one movable support which is arranged in the isolator room, the isolator room being constructed in at least two parts, the isolator room having a first boundary and a second boundary, the first boundary being fixed in position during a movement of the movable support, the second boundary being configured such that, during a movement of the movable support, the second boundary follows the movement; and
    at least one device for supplying the sterilization agent into the isolator room, the device being suitable for acting with the sterilization agent upon the parts of the apparatus that are movable relative to the device and situated inside the isolator room wherein the first boundary and the second boundary of the isolator room are closed off from an external environment by a seal arranged between the first and second boundaries so the first boundary and the second boundary are movable with respect to each other while preventing contamination of the isolator room.

2. An apparatus according to claim 1, wherein the device for supplying the sterilization agent into the isolator room has a plurality of nozzles.

3. An apparatus according to claim 1, wherein at least some of the devices for supplying the sterilization agent to the isolator room are arranged fixed in their position.

4. An apparatus according to claim 1, wherein at least some of the devices for supplying the sterilization agent to the isolator room are arranged in a movable manner.

5. An apparatus according to claim 4, wherein the movably arranged devices for supplying the sterilization agent into the isolator room are connected to a rotary distributor which is suitable for supplying the sterilization agent to the devices.

6. An apparatus according to claim 1, further comprising a central reservoir for the sterilization agent.

7. An apparatus according to claim 1, wherein the movable support is a blowing wheel with at least one blowing station, which is arranged at least in part in the interior of the isolator room.

8. An apparatus according to claim 1, wherein the sterilization agent is present in the form of a gas or liquid at the moment of injection into the isolator room.

9. An apparatus according to claim 1, wherein the isolator room has inlets for compressed air, which are suitable for permitting a high-pressure cleaning of the isolator room.

\* \* \* \* \*